United States Patent
Wu et al.

(10) Patent No.: US 10,152,762 B2
(45) Date of Patent: Dec. 11, 2018

(54) METHOD FOR DETERMINING ECOLOGICAL RISKS OF HEAVY METAL POLLUTION IN RIVER AND LAKE SEDIMENTS

(71) Applicant: Jiangsu Provincial Academy Of Environmental Science, Nanjing (CN)

(72) Inventors: Haisuo Wu, Nanjing (CN); Bing Li, Nanjing (CN); Changsheng Qu, Nanjing (CN); Shui Wang, Nanjing (CN); Wenbo Wan, Nanjing (CN); Jiayan Zhou, Nanjing (CN)

(73) Assignee: JIANGSU PROVINCIAL ACADEMY OF ENVIRONMENTAL SCIENCE, Nanking (CN)

( * ) Notice: Subject to any disclaimer, the term of this patent is extended or adjusted under 35 U.S.C. 154(b) by 381 days.

(21) Appl. No.: 14/773,493

(22) PCT Filed: Apr. 24, 2014

(86) PCT No.: PCT/CN2014/076141
§ 371 (c)(1),
(2) Date: Sep. 8, 2015

(87) PCT Pub. No.: WO2015/149408
PCT Pub. Date: Oct. 8, 2015

(65) Prior Publication Data
US 2016/0110835 A1    Apr. 21, 2016

(30) Foreign Application Priority Data

Apr. 4, 2014 (CN) .......................... 2014 1 0137454

(51) Int. Cl.
*G06Q 50/26* (2012.01)
*G01N 33/24* (2006.01)
(Continued)

(52) U.S. Cl.
CPC ........... *G06Q 50/265* (2013.01); *G01N 33/24* (2013.01); *G06F 17/18* (2013.01); *G06Q 50/22* (2013.01)

(58) Field of Classification Search
CPC ..... G06F 19/3431; G06Q 50/22; Y02W 30/95
(Continued)

(56) References Cited

U.S. PATENT DOCUMENTS 6,536,272 B1 * 3/2003 Houston .................. G01N 1/12
702/2
8,721,785 B2 * 5/2014 Mohamed ............... C04B 2/005
106/716

(Continued)

OTHER PUBLICATIONS

Zhu Hui-na, Yuan Xing-zhong, Zeng Guang-ming, Jiang Min, Liang Jie, Zhang Chang, Yin Juan, Huang Hua-jun, Liu Zhi-feng, Jiang Hong-wei, "Ecological risk assessment of heavy metals in sediments of Xiawan Port based on modified potential ecological risk index" Oct. 28, 2011, Transactions of Nonferrous Metals Society of China, 22(2012) 1470-1477.*

*Primary Examiner* — Jonathan Han
(74) *Attorney, Agent, or Firm* — Zhihua Han

(57) ABSTRACT

The present disclosure discloses a method for determining ecological risks of heavy metal pollution in sediments of river and lake. The method includes the following steps of: (1) determining concentration levels of heavy metal pollutants at different positions of water body sediments; (2) conducting statistic analysis on distribution characteristics of concentration data of various heavy metal pollutants in the water body sediments; (3) calculating an ecological risk index of a heavy metal pollutant using a formula; (4) calculating a final result of $E_r^i$; (5) drawing a distribution curve of $E_r^i$ values; (6) calculating a total ecological risk comprehensive index HRI caused by various heavy metal pollutants in the evaluated water body, and drawing a
(Continued)

cumulative probability distribution curve of HRI values; and (7) analyzing a probability that the total ecological risk comprehensive index HRI of the water body appears at different risk levels with reference to a risk level classification standard.

3 Claims, 1 Drawing Sheet

(51) Int. Cl.
*G06F 17/18* (2006.01)
*G06Q 50/22* (2018.01)

(58) Field of Classification Search
USPC .............................................................. 705/2
See application file for complete search history.

(56) References Cited

U.S. PATENT DOCUMENTS

| | | | |
|---|---|---|---|
| 2008/0195327 A1* | 8/2008 | Young | C12Q 1/6883 702/20 |
| 2012/0245858 A1* | 9/2012 | Carpenter | G01B 15/02 702/28 |
| 2014/0188495 A1* | 7/2014 | Bi | G06Q 50/22 705/2 |

* cited by examiner

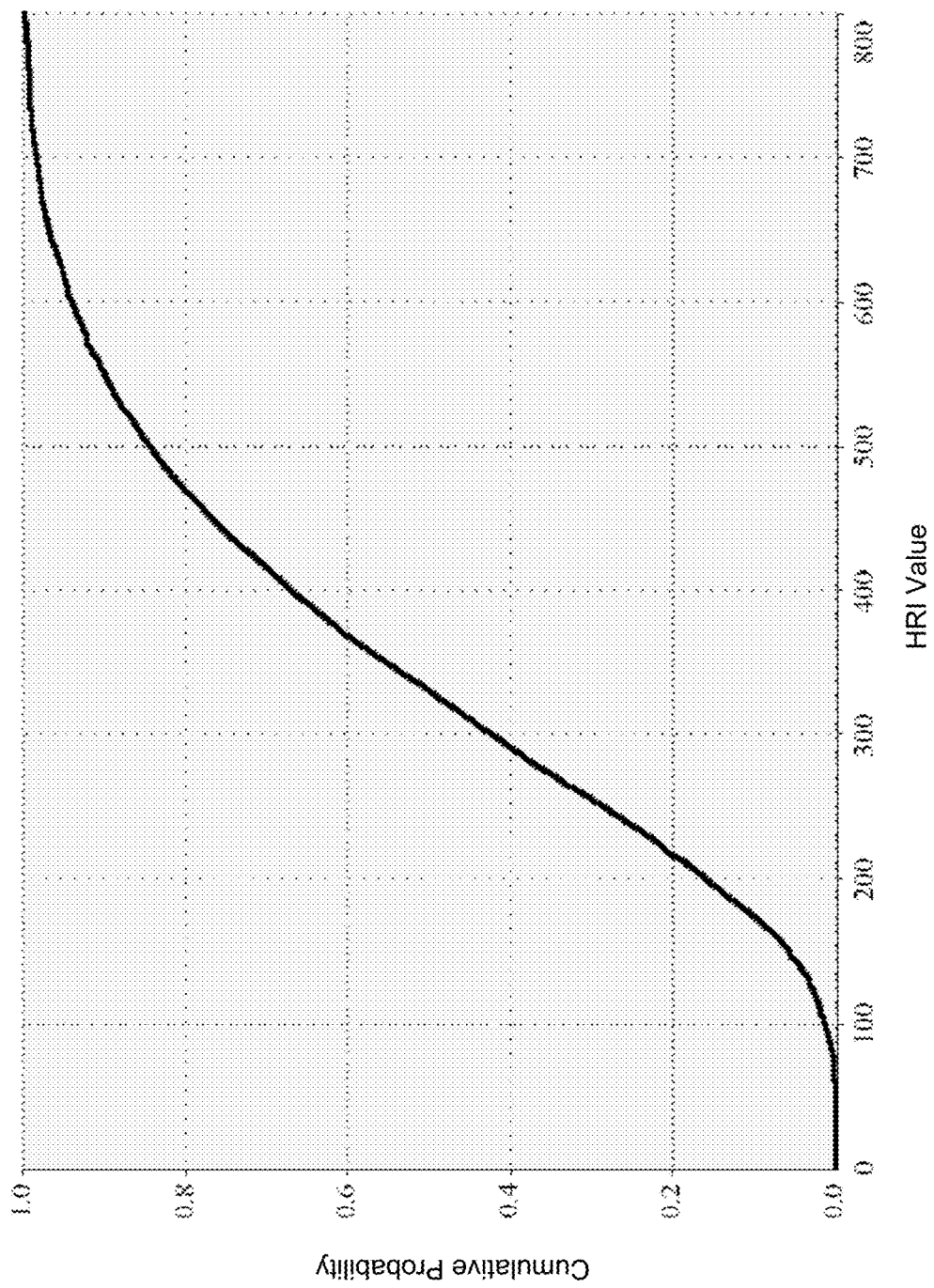

METHOD FOR DETERMINING ECOLOGICAL RISKS OF HEAVY METAL POLLUTION IN RIVER AND LAKE SEDIMENTS

CROSS REFERENCE TO RELATED APPLICATION

This application is a national stage application of International application number PCT/CN 2014/076141, filed Apr. 24, 2012, titled "A METHOD FOR DETERMINING ECOLOGICAL RISKS OF HEAVY METAL POLLUTION IN RIVER AND LAKE SEDIMENTS," which claims the priority benefit of Chinese Patent Application No. 2014101374543, filed on Apr. 4, 2014, which is hereby incorporated by reference in its entirety.

TECHNICAL FIELD

The present disclosure relates to the field of method for determining ecological risks, and more particularly, to a method for determining ecological risks of heavy metal pollution in particular to sediments of river and/or lake.

BACKGROUND

With the rapid development of urban and rural construction as well as development and utilization of minerals in China, a number of heavy metal pollutants are discharged to environmental water bodies, such as rivers and lakes, and the like. Heavy metals cannot be decomposed in water, are easily combined with other substances, and deposited into sediments at the bottom of the water body under the absorption effects of suspended matters and overlying sediments. The sediments are important parts of the ecological system in the water body, which not only provide nutrients for the organisms in the water body, but also possibly become an interior source for polluting the water body at the same time. Under certain conditions, the heavy metals enriched in the sediments will enter the water body again to cause secondary pollution, which continuously damages the ecological environment of the water body, and is harmful to the human health through a food chain. Therefore, the sediments become important objects for evaluating the pollution level of the heavy metals in the water body and the health status of the water ecological system.

US Environmental Protection Agency proposed a reference value method for risk evaluation of pollutants in ocean and estuary sediments in 1995, which mainly determines risk evaluation low value ERL (Effects range-low) and risk evaluation median value ERM (Effects range-median) according to the mass data of ocean and estuary sediments in North America; however, this method is not applicable to other regions due to territory differences. While the evaluation method for ecological risks of heavy metal pollution in river and lake sediments most widely applied internationally is a potential ecological risk index method proposed by Hankanson (a Swedish scholar), which not only considers the contents of heavy metals in bottom mud, but also associates the ecological effect and environmental effect of the heave metals with toxicology, and a comparable equivalent attribute index grading method is employed for evaluation. Some researches on the aspect of recognizing the ecological risks of heavy metals in sediments of river and/or lake are also developed in China; however, most of these researches use the potential ecological risk index method of Hankanson. Generally, we start these researches relatively late, which are still at the exploration stage.

The potential ecological risk index method of Hankanson is used as a relatively quick, simple and convenient method for dividing the sediment pollution degrees and potential ecological risks of the water body thereof, which obtains an ecological risk value by means of dividing the average concentration by the background value of the heavy metals in the sediments of the evaluated water body, and then multiplying by a toxicity regulation factor, and is a point estimation method. But actually, the concentrations of the heavy metals in the water body sediments may differ largely in different regions and time periods. The indeterminacy attribute and probability characteristics of the risk problems cannot be reflected by relying on the ecological risk value calculated according to the average concentration and the risk level division thereof. Therefore, it needs to develop a risk analysis method which can reflect the concentration fluctuation characteristics of the heavy metals in the water body sediments and the ecological risk probability attributes, so as to provide more scientific and reliable basis for rationally formulating water ecological environment protection measures.

SUMMARY

1. Technical Problems to be Solved by the Present Disclosure

With respect to the defects and problems of a conventional identification and method for determining ecological risks of heavy metal pollution in sediments on the aspect of processing indeterminacy, the present disclosure establishes a method for determining ecological risks of heavy metal pollution in sediments of river and/or lake, which conducts sampling calculation based on Monte Carlo sampling, is suitable for judging the pollution level of heavy metals in the sediments of river and/or lake and identifying the potential ecological risks, and can serve water body pollution control and water ecological management.

2. Technical Solution

The disclosure employs the following technical solution: a method for determining ecological risks of heavy metal pollution in river and lake deposits, including the following steps of:

(1) collecting water body sediment samples for detection and analysis, and determining concentration levels of heavy metal pollutants at different positions of the water body sediments;

(2) conducting statistic analysis on distribution characteristics of concentration data of various heavy metal pollutants in the water body sediments;

(3) calculating an ecological risk index of a heavy metal pollutant using a formula $E_r^i = T_r^i \times C_0^i / C_r^i$, wherein $E_r^i$ represents the ecological risk index of an $i^{th}$ heavy metal pollutant; $C_0^i$ represents the measured concentration value (mg/kg) of the $i^{th}$ heavy metal pollutant in the water body sediments; $C_r^i$ represents the background value (mg/kg) of the heavy metal pollutant before industrialization; $T_r^i$ represents the ecological toxicity coefficient of the $i^{th}$ heavy metal pollutant; and $C_r^i$ and $T_r^i$ are acquired from published literature;

(4) conducting sampling calculation using a Monte Carlo method according to the value distribution characteristics of $C_0^i$, wherein the sampling times is served as the final sampling times when the average value of $E_r^i$ is stable, i.e., the difference of the average values of the twice operations is less than 5%, and the corresponding operation result is the final result of $E_r^i$;

(5) drawing a distribution curve of $E_r^i$ values, and determining the distribution characteristics of the ecological risks of the $i^{th}$ heavy metal pollutant: analyzing a probability that the ecological risks appear at different risk levels with reference to a risk level classification standard, wherein a higher probability of the $E_r^i$ value appearing at a high risk level indicates a higher level of potential hazards caused by the heavy metal pollutant to an ecological system, and the heavy metal pollutants are more needed to be preferentially controlled;

(6) calculating a total ecological risk comprehensive index HRI caused by various heavy metal pollutants in the evaluated water body using a formula $HRI=\Sigma E_r^i$, conducting sampling calculation using a Monte Carlo sampling method, and drawing a cumulative probability distribution curve of the HRI values according to the sampling result; and (7) analyzing a probability that the total ecological risk comprehensive index HRI of the water body appears at different risk levels with reference to the risk level classification standard, wherein a higher probability that the HRI value appears at a high risk level indicates a higher level of potential hazards caused by the heavy metal pollutants in the water body to the ecological system, and heavy metal pollution abatement and water ecology supervision measures are more needed to be taken.

3. Advantageous Effects

The present disclosure provides a method for determining ecological risks of heavy metal pollution in sediments of river and/or lake, which uses a Monte Carlo sampling method to process the defects of the conventional point estimation method for processing the indeterminacy problem based on a Monte Carlo sampling theory so as to reflect the concentration fluctuation characteristics of the heavy metals in the water body sediments and the risk probability attributes, is suitable for judging the pollution level of heavy metals in the sediments of river and/or lake and identifying the potential ecological risks, and provides scientific and reliable basis for water body pollution control and water ecological management. The method can be widely applied to analysis of the ecological risks caused by the heavy metal pollutants in the water body sediments of rivers and lakes, as well as formulation of corresponding ecological environment protection measures.

BRIEF DESCRIPTION OF THE DRAWINGS

FIG. 1 is a total ecological risk cumulative probability distribution diagram of polycyclic aromatic hydrocarbons in sediments of a lake.

DETAILED DESCRIPTION OF THE PREFERRED EMBODIMENTS

The present disclosure will be further described in details hereinafter with reference to the drawings and embodiments.

Embodiment 1

Ecological risk analysis of heavy metal pollutants in sediments of a lake:

(1) The concentration data of seven heavy metal pollutants including cadmium, chromium, copper, lead, zinc, hydrargyrum and arsonium in the sediments of a lake are collected, wherein the concentration data of at least three positions is collected for each heavy metal pollutant, and a same detection and analysis method is used for the same pollutant in different positions.

(2) Statistical analysis indicates that the concentration data of various heavy metal pollutants in the water body sediments of the lake are in normal distribution, and the corresponding statistics values such as minimum, maximum, average value and standard deviation are as shown in Table 1.

(3) The ecological risk indexes of each heavy metal pollutant are calculated using a formula $E_r^i=T_r^i \times C_0^i/C_r^i$, wherein $E_r^i$ represents the ecological risk index of an $i^{th}$ heavy metal pollutant; $C_0^i$ represents the concentration (mg/kg) of the $i^{th}$ heavy metal pollutant in the water body sediments; $C_r^i$ represents the background value (mg/kg) of the heavy metal pollutant before industrialization; $T_r^i$ represents the ecological toxicity coefficient of the i heavy metal pollutant. $C_r^i$ and $T_r^i$ are from published literature (Lars Hakanson, An ecological risk index for aquatic pollution control-A sedimentological approach, 1980), as shown in Table 2.

(4) Sampling calculation is conducted using a Monte Carlo method according to the normal distribution characteristics of the value of $C_0^i$, wherein the sampling times (5000 times) is served as the final sampling times when the average value of $E_r^i$ is stable, i.e., when the difference of the average values of the twice operations is less than 5%, and the corresponding operation result is the final result of $E_r^i$.

(5) A distribution curve of $E_r^i$ values is drawn, and the distribution characteristics of the ecological risks of the $i^{th}$ heavy metal pollutant are determined: a probability that the ecological risks appear at different risk levels with reference to a risk level classification standard is analyzed, as shown in Table 3. In each pollutant, the risks of chromium, copper, lead and zinc are all low; the risks of hydrargyrum and arsonium are generally in a low-median level; and the risk of cadmium in the sediments of the lake is generally in a median-high level, and the probability of reaching the extremely high risk level is 18.1%, which indicates that the level of potential hazards caused by the cadmium in the sediments to the ecological system is higher, and the cadmium needs to be preferentially controlled.

(6). A total ecological risk comprehensive index caused by various heavy metal pollutants in the evaluated water body is calculated using a formula $HRI=\Sigma E_r^i$. Sampling conduction is conducted for 5000 times using a Monte Carlo sampling method, and a cumulative probability distribution curve of the HRI values is drawn according to the sampling result, as shown in FIG. 1.

(7) A probability that the total ecological risk comprehensive index HRI of the water body appears at different risk levels is analyzed with reference to the risk level classification standard, as shown in Table 4. The results indicate that the average HRI value is 347. If only judging according to conventional point estimation, the lake is in a median risk level. However, it can be known from the cumulative probability distribution curve of the HRI values of FIG. 1 that the probability of the HRI values in a low risk level is 5.8%, the probability of the HRI values in a lower risk level is 36.5%, the probability of the HRI values in a median risk level is 51.6%, and the probability of the HRI values in a high risk level is 6.1%. That is, the total ecological risk level of the heavy metal pollutants in the sediments of the lake is a lower-median level, which needs to be concerned to prevent the pollution from deterioration. It is apparent that the total ecological risk level of the lake is overvalued using the average value point estimation analytical method, while the method of the present disclosure determines the ecological risks caused by the heavy metal pollutants in the water body sediments of the lake more objectively and exactly.

TABLE 1

Concentration Data (mg/kg) of Heavy Metals in Sediments of a Lake

|  | Cadmium | Chromium | Copper | Lead | Zinc | Hydrargyrum | Arsonium |
|---|---|---|---|---|---|---|---|
| Minimum | 0 | 18.0 | 10.5 | 0 | 30.0 | 0.02 | 0 |
| Maximum | 23.3 | 329.0 | 90.6 | 205.9 | 8850.0 | 1.36 | 291.8 |
| Average value | 3.4 | 93.9 | 50.3 | 71.5 | 1291.1 | 0.27 | 49.7 |
| Standard deviation | 6.4 | 59.2 | 26.2 | 67.6 | 2537.2 | 0.37 | 75.1 |

TABLE 2

Background Value of Heavy Metal Pollutants before Industrialization and Ecological Toxicity Coefficient

|  | Cadmium | Chromium | Copper | Lead | Zinc | Hydrargyrum | Arsonium |
|---|---|---|---|---|---|---|---|
| $T_r^i$ | 30 | 2 | 5 | 5 | 1 | 40 | 10 |
| $C_r^i$ (mg/kg) | 1 | 90 | 50 | 70 | 175 | 0.25 | 15 |

TABLE 3

Ecological Risk Analysis Results of Each Heavy Metal Pollutant

| Value of $E_r^i$ | Risk level classification of $E_r^i$ | Probability | | | | | | |
|---|---|---|---|---|---|---|---|---|
|  |  | Cadmium | Chromium | Copper | Lead | Zinc | Hydrargyrum | Arsonium |
| $E_r^i < 40$ | Low | 10.8% | 100% | 100% | 100% | 98.4% | 30.1% | 40.2% |
| $40 \le E_r^i < 80$ | Lower | 11.5% | 0 | 0 | 0 | 1.6% | 33.5% | 36.4% |
| $80 \le E_r^i < 160$ | Median | 23.5% | 0 | 0 | 0 | 0 | 33% | 22.7% |
| $160 \le E_r^i < 320$ | High | 36.1% | 0 | 0 | 0 | 0 | 3.4% | 0.7% |
| $E_r^i \ge 320$ | Extremely high | 18.1% | 0 | 0 | 0 | 0 | 0 | 0 |

TABLE 4

Total Ecological Risk Analysis Result of the Lake

| HRI value | Risk level classification of HRI | Probability |
|---|---|---|
| HRI<150 | Low | 5.8% |
| 150 ≤ HRI < 300 | Lower | 36.5% |
| 300 ≤ HRI < 600 | Median | 51.6% |
| HRI≥600 | High | 6.1% |

What is claimed is:

1. A method for determining ecological risks of heavy metal pollution in sediments of a river or a lake, the method comprising:

(1) collecting water body sediment samples to determine concentration levels of heavy metal pollutants at different positions of the water body sediments;

(2) conducting statistic analysis on distribution characteristics of concentration data of various heavy metal pollutants in the water body sediments;

(3) calculating an ecological risk index of a heavy metal pollutant using a formula $E_r^i = T_r^i \times C_0^i / C_r^i$, wherein $E_r^i$ represents an ecological risk index of an $i^{th}$ heavy metal pollutant; $C_0^i$ represents a measured concentration value (mg/kg) of the $i^{th}$ heavy metal pollutant in the water body sediments; $C_r^i$ represents the background value (mg/kg) of the heavy metal pollutant before industrialization; and $T_r^i$ represents an ecological toxicity coefficient of the $i^{th}$ heavy metal pollutant;

(4) conducting sampling calculation using a Monte Carlo method according to value distribution characteristics of $C_0^i$, wherein the sampling times is served as final sampling times when an average value of is stable or $E_r^i$ when a difference of the average values of the two operations is less than 5%, and the corresponding operation result is a final result of $E_r^i$;

(5) determining the distribution characteristics of the ecological risks of the $i^{tph}$ heavy metal pollutant by drawing a distribution curve of $E_r^i$ values to analyze a probability that the ecological risks appear at different risk levels with reference to a risk level classification standard, wherein a higher probability of the $E_r^i$ value appearing at a high risk level indicates that a higher level of potential hazards is caused by the heavy metal pollutant to an ecological system and more necessarily the heavy metal pollutants are under control;

(6) calculating a total ecological risk comprehensive index HRI caused by the various heavy metal pollutants in the evaluated water body using a formula HRI=$\Sigma E_r^i$ to conduct the sampling calculation using the Monte Carlo method and to draw a cumulative probability distribution curve of the HRI values according to the sampling result; and (7) analyzing a probability that the total ecological risk comprehensive index HRI of the water body appears at different risk levels with reference to the risk level classification standard to determine the ecological risks of the heavy metal pollution in the sediments of the river or the lake.

2. The method of claim 1, wherein a higher probability that the HRI value appears at a high risk level in step (7) indicates a higher level of potential hazards caused by the heavy metal pollutants in the water body to the ecological system, and more necessarily heavy metal pollution abatement and water ecology supervision measures are taken.

3. The method of claim 1, further comprising:
designating the risk level to be low if a value of HRI is less than 300;
designating the risk level to be median if the value of HRI is not less than 300 but less than 600; and
designating the risk level to be high if the value of HRI is not less than 600.

* * * * *